United States Patent
Marcoux et al.

(10) Patent No.: US 10,309,904 B2
(45) Date of Patent: Jun. 4, 2019

(54) RETROREFLECTOR PROVIDING THE FUNCTIONS OF RETROREFLECTION AND PICKUP OF A PARAMETER OF THE ENVIRONMENT

(71) Applicant: COMMISSARIAT A L'ENERGIE ATOMIQUE ET AUX ENERGIES ALTERNATIVES, Paris (FR)

(72) Inventors: Pierre Marcoux, Saint Egreve (FR); Pierre Joly, Grenoble (FR); Marjorie Vrignaud, Grenoble (FR); Tarek Fathallah, Voiron (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/536,831

(22) PCT Filed: Dec. 16, 2015

(86) PCT No.: PCT/EP2015/080092
§ 371 (c)(1),
(2) Date: Jun. 16, 2017

(87) PCT Pub. No.: WO2016/097052
PCT Pub. Date: Jun. 23, 2016

(65) Prior Publication Data
US 2018/0011025 A1   Jan. 11, 2018

(30) Foreign Application Priority Data

Dec. 17, 2014  (FR) .................................... 14 62627

(51) Int. Cl.
*G01N 21/78* (2006.01)
*G02B 5/122* (2006.01)
(Continued)

(52) U.S. Cl.
CPC .......... *G01N 21/78* (2013.01); *C12Q 1/6837* (2013.01); *G01N 21/783* (2013.01);
(Continued)

(58) Field of Classification Search
CPC ...... G01N 21/78; G01N 21/783; G01N 21/80; G01N 2021/7759; G01N 2021/7773;
(Continued)

(56) References Cited

U.S. PATENT DOCUMENTS

2006/0088946 A1   4/2006   Willson et al.
2007/0036680 A1   2/2007   Hobbs et al.
(Continued)

FOREIGN PATENT DOCUMENTS

FR         2980789 A1   9/2011

OTHER PUBLICATIONS

Bennett, K.D., et al., "Temperature sensor based on light reflection from a glass/liquid boundary", "SPIE", 1996, pp. 203-214, vol. 2839.
(Continued)

*Primary Examiner* — Hina F Ayub
(74) *Attorney, Agent, or Firm* — Pearne & Gordon LLP

(57) ABSTRACT

The invention relates to a retroreflector able to be placed in contact with an environment, comprising, by way of constituent material, a material enabling a parameter of said environment to be picked up, said material modifying the optical transmission properties of the retroreflector when said parameter is present, said retroreflector being able to receive an incident light beam via a first face and to reemit a light beam via said first face.

23 Claims, 3 Drawing Sheets

(51) Int. Cl.
  *C12Q 1/6837* (2018.01)
  *G01N 33/543* (2006.01)
  *G02F 1/1335* (2006.01)
  *G02F 1/21* (2006.01)
  *G01N 21/80* (2006.01)
  *G01N 21/77* (2006.01)

(52) U.S. Cl.
  CPC ....... *G01N 33/54373* (2013.01); *G02B 5/122* (2013.01); *G02F 1/133553* (2013.01); *G02F 1/216* (2013.01); *G01N 21/80* (2013.01); *G01N 2021/7759* (2013.01); *G01N 2021/7773* (2013.01); *G01N 2021/7783* (2013.01); *G01N 2021/7796* (2013.01)

(58) Field of Classification Search
  CPC ... G01N 2021/7783; G01N 2021/7796; C12Q 1/6837; G02B 5/122; G02F 1/133553; G02F 1/216
  See application file for complete search history.

(56) References Cited

U.S. PATENT DOCUMENTS

| 2009/0141273 A1* | 6/2009 | Poulter ............... G01N 21/031 356/326 |
| 2012/0140224 A1 | 6/2012 | Switkes et al. |
| 2016/0039123 A1 | 2/2016 | Mourier et al. |

OTHER PUBLICATIONS

Guillemot, L., et al., "Facile and fast detection of bacteria via the detection of exogenous volatile metabolites released by enzymatic hydrolysis", "Phys. Chem. Chem. Phys.", 2013, pp. 15840-15844, vol. 15.

Unpublished U.S. Appl. No. 15/526,092, filed May 11, 2017.

Note: For the non-patent literature citations that no month of publication is indicated, the year of publication is more than 1 year prior to the effective filing date of the present application.

* cited by examiner

RETROREFLECTOR PROVIDING THE FUNCTIONS OF RETROREFLECTION AND PICKUP OF A PARAMETER OF THE ENVIRONMENT

CROSS-REFERENCE TO RELATED APPLICATIONS

This application is a U.S. national phase under the provisions of 35 U.S.C. § 371 of International Patent Application No. PCT/EP15/80092 filed Dec. 16, 2015, which in turn claims priority of French Patent Application No. 1462627 filed Dec. 17, 2014. The disclosures of such international patent application and French priority patent application are hereby incorporated herein by reference in their respective entireties, for all purposes.

TECHNICAL FIELD

The present invention relates to a retroreflector made in a specific material, which retroreflector gives the possibility of both ensuring retroreflection functions and capture of an operating parameter as well as a method for detecting a parameter of the environment by means of said retroreflector.

The invention thus finds application in the field of the measurement of environmental parameters, such as chemical composition, temperature or the presence of radiations, notably of ionizing radiations.

More specifically, the invention may find application in the field of monitoring the internal environment of closed spaces, such as glove boxes, fume cupboards or further of the monitoring of the environment notably for detecting atmospheric pollutants.

The invention may also find application in the detection of volatile organic compounds, notably organic volatile compounds indicating the presence of bacteria, for example in Stomacher bags, hemoculture flask, sterility tests.

STATE OF THE PRIOR ART

Retroreflectors are known optical systems which have the property of sending back light in directions close to the ones from which they stem, this property being retained for large variations of the direction of the incident beam. In other words, by means of the properties of the retroreflector, the light sent back by a source on the retroreflector is sent back towards the latter.

Also, as seen from the source or from a view point close to the source, the operating retroreflector has a particularly brilliant aspect, whence the possibility of using them for signifying objects, for example as vehicle reflectors or as reflective panels.

The return of the light on itself is particularly effective with retroreflectors may also be a benefit for measuring very accurate distances per flight time, for which one of the most known is that of the earth-moon distance which has already been evaluated by means of retroreflectors in the form of a cube corner laid on the moon.

The retroreflection properties may also be used for the indirect determination of a parameter of the environment, such as the chemical composition, the temperature or the presence of radiation, notably an ionizing radiation.

To do this, the retroreflectors are presently used according to three configurations.

According to a first configuration, as illustrated by document US 2012/0140224, the retroreflector is exclusively used for folding back the optical beam emerging from a source on itself, in order to measure the properties of a material sensitive to an environmental parameter located between the retroreflector and an instrument, which is both the light source and a detector. The sensitive material confronted with the parameter of the environment undergoes modification of its optical properties, which will give the possibility of an indirect measurement of the parameter via measurements of the light flux. In this configuration, the retroreflection function and the capture function of the parameter of the environment are fulfilled with two distinct elements from each other.

According to a second configuration, as illustrated by document US 2007/0036680, the retroreflector comprises, on its reflective surfaces, a layer in a material able to react with the environment of the retroreflector and for which the reaction modifies the reflection properties of the retroreflector. Also, in this configuration, it is necessary to modify the reflective surfaces of the retroreflector by deposition of a sensitive suitable layer to the parameter of the environment which one desires to measure. Because the sensitive material proves to be confined at a layer deposited on the reflective surfaces, the sensitivity is necessarily limited, because of the small volume of the sensitive material.

A third configuration consists of using the dependence on the environment of the reflection level upon passing from one medium to the other, which itself varies with the difference in index between both media. This type of configuration is discussed in the article «Proceedings of SPIE—The International Society for Optical Engineering 2839:203-214», wherein the different variation of the glass index and of the water index is discussed with temperature. The latter notably induces a variation of the reflection level of the surfaces of a cube corner of glass immersed in pure water for measuring its temperature. Also, for measuring the environmental parameter, which is here temperature, it is necessary to produce the retroreflector in a material having well known index variation properties and to place it in a known medium, here pure water, also having well known properties of index variation and mainly dependent on the parameter to be measured.

In view of what exists, the authors of the invention therefore set their goal to develop novel retroreflectors which give the possibility of ensuring, in addition to retroreflection of light rays, the detection of a parameter of the environment without it being necessary notably, to use distinct elements for ensuring its two functions or for resorting to the deposition of a specific capture layer on the surface of the retroreflector.

DISCUSSION OF THE INVENTION

Thus, the invention relates to a retroreflector able to be placed in contact with an environment, comprising, as a constitutive material, a material for capturing a parameter of said environment, said material inducing a modification of the optical transmission properties of the retroreflector in the presence of said parameter and said retroreflector being able to receive an incident light beam through a first face and of emitting a light beam through said first face (i.e. in other words, said retroreflector is able to receive an incident light beam and to send it back through the same face).

It is specified that, by capturing a parameter of the environment, is meant a detection of the presence of this parameter.

It is specified that, per constitutive material, the material making up the retroreflector, i.e. the material comprised between the faces of the retroreflector and also delimiting the latter.

Also, by means of the characteristics of the constitutive material of the retroreflector of the invention, the functions of retroreflection and of capture of a parameter of the environment are ensured by the retroreflector as such, without it being necessary:

- to use two distinct elements, as this is the case of the first configuration mentioned above, which makes the design of the retroreflectors more simple;
- to deposit a specific capture layer at the surface of the retroreflector, as this is the case of the second configuration mentioned above.

According to the invention, from a structural point of view, the retroreflectors of the invention advantageously have three first faces, said rear faces defining a trihedron, said three faces being convergent in a point forming an apex of the trihedron, and a fourth face, a so called front face, opposite to said apex of the trihedron and containing said trihedron, said material extending between these faces.

In other words, the retroreflector has three of its faces converging in a point forming an apex of the retroreflector and a fourth face opposite to said apex, the resulting shape comprising, as a constitutive material, a material for capturing a parameter of the environment as defined above.

More specifically, the retroreflectors of the invention may be characterized in that each aforementioned rear face respectively extends along a first plane, a second plane and a third plane, said planes being substantially orthogonal to each other pair wise, i.e. they form between them an angle comprised between 80° and 100°, preferably between 85° and 95°. Advantageously, with this configuration, the light beam emerges along a direction substantially parallel to that of the incident light beam.

Still more specifically, the retroreflectors may have a shape of a cube corner, i.e. a shape comprising three orthogonal faces pair wise and a fourth face containing the volume delimited by these three orthogonal faces and which has the particularity that any incident ray corresponds to a reflected ray in the same direction but in the opposite sense.

In particular, when the retroreflector has a cube corner shape, there is a maximization of the length of the optical path of the light beam relatively to a so called transmission configuration, in which the material would be positioned between a light source and the detector. Indeed, the path in a cube corner with a thickness L (distance between the front face and the apex) is equivalent to the rectilinear path in a disc of thickness 2 L. This gives the possibility of improving the detection sensitivity.

It is then possible to characterize a medium contained in a chamber without any confinement rupture, as illustrated in FIG. 6 relative to example 1.

From the point of view of the operation, as mentioned above, because of its retroreflection function, the retroreflector is able to receive an incident light beam and to send it back through the same face.

As compared with the specific geometry mentioned above, the retroreflector is more particularly able to receive an incident light beam through said front face, said beam being centered along a first direction and is able to divert said light beam when the light beam propagates in said material, so as to send back the light beam, through said front face, according to a second direction parallel to said first direction.

This operating principle is again taken in FIG. 1 added as an appendix illustrating a retroreflector 1 comprising 3 rear faces (numbered as 3) and a front face (numbered as 5), the incident and reflected beam being represented by number 7.

As mentioned above, in the contact of an environment for which a parameter is intended to be determined, the material capturing a constitutive parameter of the environment of the retroreflector is able to modify the optical transmission properties of the retroreflector in the presence of said parameter. More specifically, the capture material, in the presence of said parameter, may induce, advantageously a modification of the light intensity of a light beam sent back by said retroreflector in the presence of said parameter relatively to the case when the retroreflector is not in the presence of said parameter. In this case, from a practical point of view, the modification of the optical transmission properties may be determined by measuring the ratio between the light intensity of the incident beam and the light intensity of the beam sent back by the retroreflector.

Generally, the capture material should be porous or pervious or able to change aspect under the effect of temperature or radiation.

By changing aspect, is meant a modification of the optical transmission property able to be modified, in a given wavelength range, when the retroreflector is placed in contact with a parameter of an environment (for example, presence of a gas, temperature, ionizing radiation, for example, gamma radiation or X radiation).

Thus, the parameter, whether this is a molecule, a temperature or a radiation penetrates into the material, inducing a variation in the optical transmission.

The capture material of a parameter of the environment is advantageously, a porous material and more specifically a material with open porosity, i.e. a porosity allowing communication between the various pores.

Advantageously, the capture material is also a transparent material.

These characteristics of porosity quite particularly find their significance, when the parameter of the environment to be captured is a gas, and more specifically, a volatile organic compound. The porosity thus gives the possibility to the gas of penetrating into the volume of the retroreflector, in order to modify the transmission thereof after capturing this gas with the constitutive capture material of the retroreflector.

Advantageously, the porosity defined as the fraction of the free volume relatively to the total volume of the material (i.e. the ratio (free volume/total volume)) is comprised between 2% and 80%, this porosity being determined by adsorption-desorption measurement of nitrogen at 77K.

Advantageously, the capture material may have a specific surface area ranging from 100 to 5,000 $m^2/g$.

When the capture material of the retroreflector is a porous material intended for capturing a gas (which is the parameter of the environment), the constitutive material has advantageously a high refractive index for compensating for the loss of value of the refractive index of the porous material related to the fact that the pores filled with gas have a refractive index close to 1, which causes a reduction in the refractive index of the porous material.

Independently of the porosity of the material, the material of the retroreflector may have, advantageously, a refractive index ranging from 1.2 to 2, this refractive index may be measured by a method involving a microscope, as discussed in part d) of example 1.

When the capture material of the retroreflector is a porous material intended for capturing a liquid, such as an aqueous environment of index 1.33, (which is the parameter of the environment), the capture material may advantageously have a refractive index ranging from 1.66 to 2.7, this refractive index may be measured by a method involving a microscope, as discussed in part d) of example 1.

The ratio between the index of the material and the index of the medium to be characterized is comprised between 1.2 and 2. In the case of a gas, the index of the material is advantageously comprised between 1.2 and 2, since the index of the medium is 1. The index of the material over the index of the medium to be characterized may be defined as a relative index.

The higher the index ratio, the more the direction of the reflected and incident beam may deviate from the normal to the front face of the retroreflector, the latter being the face crossed by the incident beam and the reflected beam.

From the point of view of its composition, the capture material of a parameter of the environment may be in an organic or inorganic material, preferably forming a matrix, comprising, inside one or several compounds, generally organic, bearing one or several groups fulfilling a capture function of a parameter of the environment, this formulation covering two conceivable alternatives:
  a first alternative wherein the compound(s) bearing one or several groups are included in the organic or inorganic material without being bound in a covalent way to the latter;
  a second alternative wherein the compound(s) bearing one or several groups are bound, covalently, to said organic or inorganic material.

According to this second alternative, when the compound(s) bearing one or several groups are bound covalently, to an inorganic material, the resulting material is an inorganic-organic hybrid material.

Independently of the aforementioned alternative:
  when the material forming a matrix is an organic material, this may be a material in at least one polymer, for example a material in polydimethysiloxane (known under the acronym of PDMS), which has the capability of being pervious to gases and the capability of being machined by molding; and
  when the material forming a matrix is an inorganic material, this may be a material of the inorganic oxide type and, advantageously a material of the oxide(s) type of a metal element and/or of a metalloid element (such as Si).

Advantageously, the material of the inorganic oxide(s) type comprises one or several oxides of an element selected from among silicon, titanium, zirconium, aluminium, vanadium, chromium, yttrium, tungsten, niobium, molybdenum.

Even more specifically, the material of the inorganic oxide(s) type may comprise silica and an oxide having a higher refractive index than silica, this oxide may be selected from among zirconia, titanium oxide.

This material of the inorganic oxide(s) type may advantageously be a sol-gel material.

By "sol-gel material", is meant conventionally a material obtained by a sol-gel method consisting of using as precursors, for example alkoxides, either identical or different, of formula $M(OR)_n(R')_m$, wherein M is a chemical element such as silicon (Si), titanium (Ti), zirconium (Zr), vanadium (V), tungsten (W), molybdenum (Mo), chromium (Cr), niobium (Nb), aluminium (Al), yttrium (Y), R and R' representing an alkyl group, n being a positive integer and m being equal to 0 or being a positive integer, the sum (m+n) corresponding to the valency level of M.

The sol-gel materials are generally prepared in a solvent, which is preferably miscible with water and may be gradually evaporated and under mild conditions, in which the precursors are soluble.

In the case of silicon alkoxides, mention may notably be made, as a solvent, of alcohols, such as methanol, ethanol; ethers, such as diethylether and tetrahydrofurane; chlorinated solvents, such as chloroform, $CH_2Cl_2$, $C_2H_5Cl_2$, other aprotic solvents like acetonitrile, acetone, methylethylketone, or dioxane or other protic solvents like acetic acid, formamide.

In the presence of water, the hydrolysis of the alkoxide groups (—OR) intervenes and the latter are transformed into silanol groups (M-OH) which condense by forming siloxane groups (M-O-M). Small particles with a size generally less than 1 nanometer are then formed. They aggregate and form loose clusters in suspension in the liquid: this is the sol. As the polycondensation continues over time, the viscosity of the sol increases until gelling: the sol becomes a gel.

A solid sol-gel material is then obtained by drying the gel, called a xerogel. During this step, the residual and interstitial solvents escape from the formed polymeric lattice and evaporate, which causes the contraction of the material, notably by a factor 2 on each of the dimensions relatively to the sol. A final material is therefore obtained for which the volume is reduced as compared with the volume occupied by the sol.

The sol-gel materials may be classified according to the pore size. Indeed, according to rules established by the International Union of Pure & Applied Chemistry (IUPAC) it is possible to distinguish, according to the average diameter of the pores in a material, the micropores (less than 20 Å), the mesopores (20-500 Å) and the macropores (more than 500 Å).

As mentioned below, the capture material for a parameter of the environment may be an organic or inorganic material, preferably forming a matrix, comprising, inside, one or several generally organic compounds bearing one or several groups fulfilling a function for capturing a parameter of the environment (said to be later on a specific group), this parameter of the environment may be:
  the chemical composition of the environment, for example the presence in the environment of chemical compounds, such as atmospheric pollutants, volatile organic compounds, known under the name of "VOC";
  the temperature of the environment;
  the presence of radiation in the environment, in particular an ionizing radiation, for example an X radiation or y radiation.

For these two latter parameters, the detection of the temperature and of the radiation may be intrinsic to the material, without it being necessary to add specific sensors.

More specifically, the mechanism for capturing the parameter of the environment by the aforementioned group(s) may respond to the following schemes:
  a capture of the parameter of the environment by chemical modification of the specific group(s), which may be the case when the parameter is a chemical compound which chemically reacts with the aforementioned group(s) or even when the parameter is a physical parameter, such as the temperature or radiations, which may induce a chemical modification of the aforementioned groups;
  a capture of the parameter of the environment by chemical affinity between the specific group(s) and the parameter of the environment, which may be the case when the parameter of the environment is a chemical compound having chemical affinity with the aforementioned group (s) (for example, from the point of view of hydrophilicity or hydrophobicity) for example, by establishment of weak bonds between the aforementioned group(s) and the chemical compound without this inducing any chemical modifications of the aforementioned group(s) and of the chemical compound; and a combination of a capture of the parameter by chemical modification of the specific group(s) of the organic compound and of a capture of the parameter by chemical affinity between the specific group(s) of the organic compound and the chemical compound.

In other words, when the parameter of the environment is a chemical compound, the compound(s) generally organic, bearing one or several groups fulfilling a function for capturing a parameter of the environment may have one or several groups able to capture said chemical compound with chemical modification of the latter and/or able to capture said chemical compound by chemical affinity without any chemical modification of the chemical compound.

Regardless of the mechanism set into play, the material of the retroreflector, in contact with the parameter of the environment which one desires to determine (presence of a gas, ionizing radiation, such as y radiation or X radiation), may be led to changing color, i.e. undergoing a modification of its optical transmission properties in a given range of wavelengths.

More specifically, when the parameter of the environment is a chemical compound able to chemically modify the compound(s), generally organic, comprised in the material, this chemical modification may result from an acid-base reaction between the chemical compound and the specific group(s) of the compound(s), generally organic, comprised in the material. This or these specific group(s) may be a proton attractor group, when the chemical compound comprises a proton donor group, or may be a proton donor group when the chemical compound comprises a proton attractor group.

This chemical modification may also result from a covalent reaction between the chemical compound and the specific group(s) comprised within the material, in which case a covalent bond results between said chemical compound and the specific group(s). The organic compound comprising at least such a specific group within the material may thus be described as a probe molecule.

More specifically, when the parameter of the environment is a chemical compound which has a chemical affinity for the generally organic compound(s), comprised in the material, the specific group (s) of the generally organic compound (s), comprised in the material may be:

Hydrophobic groups, when the chemical compound comprises a hydrophobic group, for example, such as a hydrocarbon group; and Hydrophilic groups, when the chemical compound comprises a hydrophilic group, for example, such as an OH group.

As mentioned above, there may be both a combination of a capture of the parameter by a chemical modification of the specific group(s) of the organic compound and a capture of the parameter by chemical affinity with the specific group (s) of the organic compound.

In this case, the compound comprised within the material is advantageously a bearer of at least one group fulfilling a function for capture of a parameter of the environment by chemical modification of said group by the parameter of the environment (such as a chemical compound) and at least one group for filling a function of capturing a parameter of the environment by chemical affinity with the parameter of the environment (such as a chemical compound) with said group.

Also, the compound comprised within the material may comprise:

A hydrocarbon group, such as an alkylene group, which conventionally fulfils a hydrophobic function, which may allow attraction, by chemical affinity of a hydrophobic chemical compound; and A proton-attractor group, such as an amine group, which will be capable of chemically reacting with a proton of the same chemical compound.

Such an organic compound may be represented, when it is bond covalently to the inorganic or organic oxide material type, with the following formula:

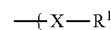

Wherein:
X represents an hydrocarbon group of the alkylene-type; and
$R^1$ represents a proton-attractor group, such as a primary amine group,
the brace indicating the position through which the compound is bond covalently, to the material of the inorganic or organic oxide type.

Independently of the capture mechanism, the capture phenomenon of the parameter of the environment, because it occurs within the material, induces a modification of optical transmission properties of the constituent material of the retroreflector in its volume, this change in the optical transmission property is then used for allow an indirect measurement of the relevant parameter via measurements of light flux.

According to a particular embodiment of the invention, the retroreflectors of the invention may be retroreflectors for which capture material comprises a material comprising a silica and at least one other oxide of an element selected from among titanium, zirconium, aluminium, vanadium, chromium, yttrium, tungsten, niobium, molybdenum, a portion of the silicon atoms being bond covalently to an organic compound bearing one or more groups fulfilling a function for capturing a parameter of the environment.

Still more specifically, according to this particular embodiment, the retroreflectors of the invention may be retroreflectors for which the capture material comprises silica and at least one other oxide of an element selected from among zirconium, titanium.

Still more specifically, according to this particular embodiment, the organic compound bearing one or more groups fulfilling a capture function of a parameter of the environment fits the following formula:

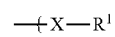

Wherein:
X represents a hydrocarbon group of the alkylene-type; and
$R^1$ represents a proton-attractor group, such as a primary amine group,
the brace indicating the location for which the compound is bond, covalently, to a portion of the silicon atoms of the silica.

For the embodiment mentioned above, the retroreflectors are particularly adapted for the detecting of a volatile organic compound having an acid nature such as orthonitrophenol.

Alternatively, mention may be made; as an organic compound bearing one or several groups fulfilling a function for capturing a parameter of the environmental, the following compounds:

compounds belonging to the category of coloured pH indicators, such as bromothymol blue, bromophenol blue, thymol blue, bromothymol blue being notably capable of detecting carbonic acid;

compounds belonging to the category of solvate-chromic probes, i.e. compounds which change color depending on the polarity of the medium in which they are found, such as malachite green, Brilliant Yellow, Reichardt's Dye (or Reichardt coloring agent able to detect polar molecules, such as acetonitrile and hydrocyanic acid);

Organic compounds belonging to the family of aldehydes, such as dimethylaminocinnamaldehyde for the detection of indole and β-naphthylamine;

Organic compounds belonging to the family of disulfides, such as 5, 5'-dithiobis-(2-nitrobenzoic acid) for detecting sulfide compounds or dithionitrobenzoic acid for the detection of $H_2S$;

Organic compounds belonging to the family of primary amines, such as 3-aminopropyl for the detection of nitrophenols;

Organic compounds belonging to the family of carboxylic acids, such as isovaleric acid; and Organic compounds belonging to the family of ketones, such as 4-amino-3-penten-2-one for the detection of formaldehyde.

These different compounds may notably be used for determining a parameter of the volatile organic compound type, these compounds may fulfil the role of revelation factors, which ensure modification of the absorbance of the retroreflector, in which they are contained.

The retroreflectors of the invention are intended, as indicated by their name, for reflecting incident light while allowing the detection of a parameter of the environment, such as a volatile organic compound present in the environment by means of the capability of the capture material of modifying the optical transmission properties of the retroreflector, and more specifically, for example, inducing a modification of the light intensity of a light beam sent back by said retroreflector in the presence of said parameter of the environment relatively to the light intensity of the incident light beam.

Also the invention also relates to a method for detecting at least one parameter of the environment, comprising the following steps:

a step for contacting a retroreflector of the invention with an environment, for which a given parameter is intended to be detected;

a step for illumination of the retroreflector with a first light beam having a first wavelength, said first wavelength corresponding to a wavelength which may cause a variation of the optical transmission of the material making up the retroreflector after capture of the parameter of the environment;

a step of analyzing a first light beam reflected by the retroreflector, from which is inferred if necessary, the presence of said parameter of the environment.

Said first light beam may include a plurality of wavelength and the step for analyzing the reflected beam may comprise an analysis of said beam with at least two wavelengths of said plurality of wavelengths.

Further, the method may also comprise the following steps:

a second step for illuminating the retroreflector with the light beam comprising a second wavelength, said second wavelength corresponding to a wavelength which may cause a second variation in the optical transmission of the material making up the retroreflector after capturing of the parameter of the environmental, said second variation being less than said first variation;

a step for analyzing a second light beam reflected by the retroreflector;

a step for comparing said first and second reflected beams, from which, is inferred if necessary, the presence of the parameter of the environment.

For example, when the material capturing the parameter of the environment is able, in the presence of the parameter of the environment which is intended to be detected, of modifying the light intensity of the light beam reflected relatively to that of the incident light beam, the analysis step may consist, in a first phase, of measuring the light intensity of the reflected beam and then, in a second phase, comparing it with the intensity of the light beam of the illumination step, so as to make the correlation with the presence of the parameter of the environment.

As an example, for the detection of a parameter of the environment, such as a specific VOC, the retroreflector is illuminated, during the illumination step, with an illumination device, for example one or several light-emitting diodes (LEDs) emitting incident rays at at least one wavelength able to be absorbed by the volatile organic compound which is intended to be detected, the optional presence and optionally emitting incident rays at at least one other length acting as a reference wavelength. A measuring device, such as a colour camera, ensures the measurement of the intensity of the rays at the reflected aforementioned wavelengths by the retroreflector. Also, the detection of the volatile organic compound captured by the retroreflector may be materialized, during the analysis step, by a reduction in the intensity of the reflected ray having the wavelength of absorption of the volatile organic compound, while the light intensity of the reflected ray having the reference wavelength remains constant.

More specifically, when the retroreflector is targeted at detecting a volatile organic compound emitted by a bacterium subsequently to hydrolysis of a given enzymatic substrate, the detection as such may be achieved after incubation on a model similar to discussed in the previous paragraph (i.e. with the use of two wavelengths: one specific wavelength and one reference wavelength) or by a kinetic monitoring, i.e. a tracking at one single specific wavelength before and after the introduction of the enzymatic substrate. Practically, the retroreflectors of the invention may be used for detecting bacteria in a liquid, for example a body liquid, and notably blood, by positioning the retroreflector in a plug, in such a way that the main face is accessible from the outside. It is then possible to detect the presence of orthonitrophenol between the liquid and the retroreflector, which expresses the presence of a microorganism in the body liquid.

More generally, this application may be transposed to any product, either solid or liquid, for which the sterility is intended to be controlled.

When the retroreflector is targeted at detecting a parameter of the environment of a volume (for example, a volume contained in a chamber) for which the characteristics are intended to be determined, the retroreflector may be placed on the internal face of the wall of the volume, it being understood that the wall has to be transparent to the light used for examining the retroreflector. Thus it is possible to have the advantage of placing all the read out instrumentation of the retroreflector (emission and detection of the light beam) in front of the main face of the retroreflector and not on either side of the latter.

When the retroreflector comprises a capture material comprising a material of the inorganic oxide (s) type, it may be prepared for a method via a sol-gel route comprising the following steps:

a) a step for filling the internal cavity of a mold, said internal cavity having a shape matching that of the retroreflector which one desires to obtain with a sol-gel solution;

b) a step for gelling the sol-gel solution in the mold; and c) a step for drying in said mold the gel obtained in b), in the term for which said gel is transformed into a constituent material of the retroreflector.

Details relating to the application of these steps may be found in the application FR 2 980 789, incorporated herein by reference.

As mentioned above, it is introduced, into the internal cavity until complete filling of the latter, with a sol-gel solution.

This sol-gel solution may also be prepared prior to step a).

This preparation step may consist of putting into contact one or several molecular precursors of a metal element and/or of a metalloid element, a generally organic compound bearing one or several groups fulfilling a function for capturing a parameter of the environment or a precursor of the latter and optionally of other adjuvants, such as water, a complexing agent of at least one of the said precursors, with a medium comprising one or several organic solvents.

The molecular precursors of a metal element and/or a metalloid element may appear, more generally as organometallic compounds of metal elements and/or metalloid elements, such that, notably, alkoxides, for example, those fitting the formula $(R^2O)_nM$ or $R^3M(OR^4)_{n-1}$, wherein M refers to the metal elements and/or the metalloid elements, n represents the degree of oxidation of M and $R^2$, $R^3$ and $R^4$ represent, independently of one another, a linear or branched alkyl group which may include from 1 to 10 carbon atoms or a phenyl group.

The general organic compound bearing one or several groups fulfilling a function for capturing a parameter of the environment, as mentioned above, may be understood within the material without there being any covalent bonds between the inorganic oxide (first case) and said compound or may be bond covalently to said inorganic oxide (second case).

According to the first case, the aforementioned generally organic compound may be directly included in the sol-gel solution during its preparation method, this compound not reacting during step b) with the aforementioned precursors. After gelling of the sol-gel solution, it is again directly found confined by encapsulation within the gel, without there being any covalent bond between the compound and the constitutive units of the gel.

According to the second case, the aforementioned generally organic compound may be introduced, during the preparation of the sol-gel solution, directly via a precursor of formula $R^5M(OR^6)_{n-1}$ where M being as defined above, $R^6$ representing a linear or branched alkyl group, which may include from 1 to 10 carbon atoms or a phenyl group, $R^5$ corresponding to the organic compound and n corresponding to the degree of valence of M. During the step for gelling the sol-gel solution, the precursor of formula $R^5M(OR^6)_{n-1}$ reacts with the other aforementioned precursors in order to form an oxide lattice incorporating the element M of the precursor of formula $R^5M(OR^6)_{n-1}$, this element M being found in the lattice covalently bonded to the group $R^5$, which is the organic compound.

As an example, when M corresponds to the silicon element, mention may be made, as a precursor, of 3-aminopropyltriethoxysilane (APTES, $Si(C_3H_6NH_2)(OC_2H_5)_3$), 3-aminobutyltriethoxysilane (ABTES, $Si(C_4H_8NH_2)(OC_2H_5)_3$), 3-aminopropyltrimethoxysilane (APTMS, $Si(C_3H_6NH_2)(OCH_3)_3$), (3-(methylamino)propyl) trimethoxysilane ($Si(C_3H_6NHCH_3)(OCH_3)_3$), 3-carboxypropyltriethoxysilane ($Si(C_3H_6CO_2H)(OC_2H_5)_3$), 3-carboxypropyltrimethoxysilane ($Si(C_3H_6CO_2H)(OCH_3)_3$), 1,2-bis(triethoxysilyl) ethane (($OC_2H_5)_3Si-CH_2-CH_2-Si(OC_2H_5)_3$), 1,2-bis(trimethoxysilyl) ethane (($OCH_3)_3Si-CH_2-CH_2-Si(OCH_3)_3$), (3,3,3-trichloropropyl) triethoxysilane ($Si(C_2H_5CCl_3)(OC_2H_5)_3$) and 3,3,3-trifluoropropyl trimethoxysilane ($Si(C_2H_5CF_3)(OCH_3)_3$) and mixtures thereof.

Preferably, the solvent is an organic solvent selected from among:

Saturated or unsaturated aliphatic or aromatic monoalcohols, for example, those of formulae R"—OH, wherein R" represents a linear or branched alkyl group, comprising from 1 to 30 carbon atoms, preferably from 1 to 10 carbon atoms or a group phenyl;

Diols, for example, those of formula HO—R'"—OH, wherein R'" represents a linear or branched alkylene group comprising from 1 to 30 carbon atoms, preferably from 1 to 10 carbon atoms, or a phenylene group.

As examples of diols, mention may be made of ethylene glycol, diethylene glycol or further triethylene glycol.

In addition to the presence of one or several molecular precursors and of one or several organic solvents as defined above, the sol-gel solution may comprise other adjuvants, such as:

Water, which may contribute to facilitate the gelling process of the sol-gel solution;

Catalysts giving the possibility of accelerating the kinetics of the hydrolysis and condensation reactions during the transformation of the sol-gel solution into a gel (these catalysts may be an inorganic acid, such as hydrochloric acid, an organic acid, such as acetic acid);

Complexing agents of at least one of said precursors, with a view for example of slowing down the hydrolysis of certain precursors, like precursors based on zirconium or based on titanium which hydrolyze very rapidly because of the significant positive partial charge on the metallic element.

As examples of complexing agents, mention may be made of acetic acid, acetylacetone or 2-methoxyethanol.

As an example, when the retroreflector comprises, as a constituent material, a material comprising silica and at least one other oxide of an element selected from among zirconium, titanium and comprises, as organic compound bearing one or several groups fulfilling a function for capturing a parameter of the environment, a compound fitting the following formula:

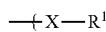

Wherein:

X represents a hydrocarbon group of the alkaline type; and $R^1$ represents a proton-attractor group, such as a primary amine group.

the brace indicating the location for which the compound is bond covalently to a portion of the silicon atoms of the silica, the method for preparing the sol-gel solution may comprise the following steps:

d) a step for putting into contact an alkoxysilane of formula $(R^2O)_4Si$ or $R^3Si(OR^4)_3$ with $R^2$, $R^3$ and $R^4$ being such as defined above, with an organic solvent and optionally water, in return for which a first solution is obtained;

e) a step for putting into contact an alkoxy silane of formula $(R^2O)_nM$ or $R^3M(OR^4)_{n-1}$ with M being Ti or Zr and $R^2$, $R^3$, $R^4$ and n being as defined above with a complexing agent of M, preferably selected from among acetic acid, acetylacetone or 2-methoxyethanol, in return for which a second solution is obtained;

f) a step for putting into contact said first solution and said second solution;

g) a step for adding to the mixture resulting from step c) an alkoxysilane of formula $R^5Si(OR^6)_3$ with $R^6$ being such as defined above and $R^5$ corresponding to the formula:

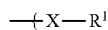

X and $R^1$ being as defined above.

The sol-gel solution obtained at the end of step d) is subsequently used directly for applying the method for preparing a retroreflector as defined above.

When the retroreflector comprises a sensor material comprising an organic material of the polymer type and one or several compounds, generally organic, bearing one or several sensor functions, said compound(s) not being bond covalently to the organic material, may be prepared according to the following method:

A method implying a polymerization step, in a mold for which the shape corresponds to the shape of the retroreflector, of a mixture comprising one or several monomers and the generally organic compound(s), bearing one or several groups fulfilling the function of capturing the parameter of the environment (said to be below a first alternative);

A method implying a polymerization step, in a mold for which the shape corresponds to the shape of the retroreflector, of a mixture comprising one or several precursor monomers, of said polymer followed by a step for doping the polymer obtained by the compound (s), generally organic, bearing one or several groups fulfilling the function of capturing the parameter of the environment (said below a second alternative).

The first variant is particularly adapted for the polymerizable materials which may be obtained by polymerization at room temperature, such a temperature giving the possibility of avoiding degradation of the aforementioned component(s).

The second alternative is particularly adapted for porous polymeric materials, wherein it is possible, after polymerization, of incorporating by doping the aforementioned compound(s) (for example, probe molecules able to modify the transmission in a given range of wavelengths), for example, according to an amount which may be less than 10% by mass.

More specifically, mention may be made, as a polymeric material, a polydimethysiloxane material (also referred to as PDMS) having the property of being pervious to gases. Because of its preciousness to gases, it is possible to incorporate the organic compound(s) bearing one or several groups fulfilling the capturing function by impregnating in a gas form of the PDMS polymerized beforehand at high temperatures.

Other features and advantages of the invention will become apparent from the description supplement which follows, which relates to an example for preparing a retroreflector according to the method of the invention.

Of course, this description supplement is only given as an illustration of the invention and by no means forms a limitation.

SHORT DESCRIPTION OF THE DRAWINGS

DETAILED DISCUSSION OF PARTICULAR EMBODIMENTS

Example 1

This example illustrates the preparation via a sol-gel route of a retroreflector according to the invention, this retroreflector having a cube corner shape or more specifically a shape comprising three perpendicular flat faces planes relatively to each other and curvilinear face connecting the apices of the perpendicular faces.

To do this, the preparation of the retroreflector occurs in three steps:

a first step for preparing the mold (said to be below step a);

a step for preparing the sol-gel solution (said to be below step b);

a step for manufacturing the retroreflector as such (said to be below step c).

Finally, this example includes a portion relative to the characterization of the constitutive xerogel of the retroreflector (said below to be step d).

a) Step for Preparing the Mold

Figure 1:
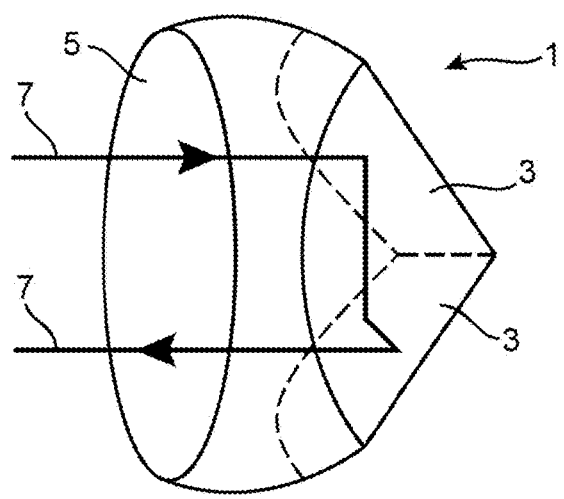
FIG. 1 shows a cross-sectional view of a retroreflector according to the invention having a cube-corner shape.
Figure 2:
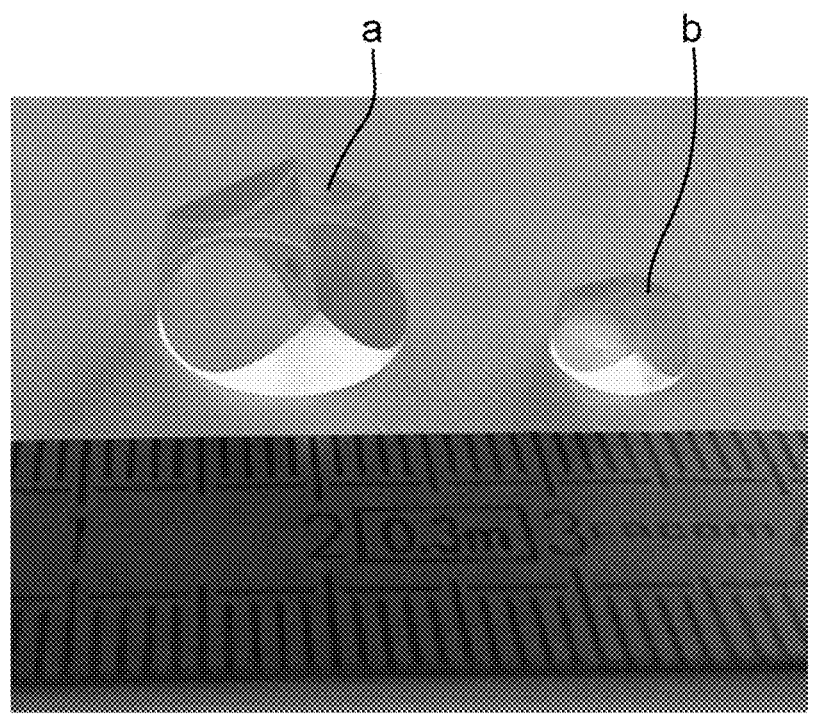
FIG. 2 illustrates a photograph as a top view of the retroreflector obtained in example 1 (portion b) and of its model (portion a).

The model used for the manufacturing of the mold is illustrated by portion a) of FIG. 2, which appears as a shape comprising two flat faces perpendicular to each other and a third curvilinear face connecting the apices of both perpendicular faces.

The mold is prepared by the succession of the following operations:

1—Preparation by means of a spatula of a mixture of two components, respectively polydimethylsiloxane (PDMS) and a cross-linking agent according to a ratio of 10/1 (these components being available from Dow-Corning under the name of SylGard 184);

2—Casting this mixture in a plexiglass container over a height of 1.5 mm thickness;

3—Cross-linking of the thereby cast mixture for 2 hours at 80° C.;

4—Placing the aforementioned model on the thereby cross-linked mixture;

5—Casting the mixture defined in point 1 above on the model until it is completely covered;

6—Cross-linking of the thereby cast mixture for 2 hours at 80° C.;

7—Manual removal of the plexiglass container from the mold, thereby obtained;

8—Opening the mold in PDMS into two portions by means of a scalpel in order to remove the initial model taken in the PDMS mold.

Both portions of the PDMS mold are then collected after plasma activation according to the following conditions:

1—Both portions of the mold are placed in an $O_2$ plasma (Plasma $O_2$ AST Product Inc), the following conditions being applied for activating the surface functions of the PDMS ($PO_2$ 1 bar; Power 100 Watt; Duration 1 minute; Adaptation 50-50% network; Gas 120; Gas flow 60; Operating point 0.5);

2—After applying the plasma, both surfaces of the mold to be adhesively bound are put into contact. A pressure is exerted for improving the contact between both surfaces and thereby improving the adhesive bonding.

Both portions of the mold are thus adhesively bound, in return for which a mold is obtained having an internal cavity corresponding to the shape of the object to be molded.

b) Step for the Preparation of the Sol-Gel Solution

The sol-gel solution is prepared by the following succession of operations:

1—Preparation of a solution 1: Mixing at room temperature for 4 hours with stirring of 0.885 ml of tetramethylorthosilicate (obtained from the supplier Sigma-Aldrich), of 2.5 ml of methanol and 0.432 ml of water, to which are added 4 ml of anhydrous ethanol and then 4 ml of 1M hydrochloric acid with stirring;

2—Preparation of a solution 2: Mixing at room temperature for 4 hours with stirring of 0.75 mL of zirconium n-propoxide and of acetic acid (0.25 ml);

3—Mixing at −20° C. the solution 1 and the solution 2 and addition of 0.5 mL of 4-aminobutyltriethoxysilane (obtained from the supplier ABCR).

c) Manufacturing of the Retroreflector as Such

The sol-gel solution obtained in step b) is then introduced into the mold defined in step a). This solution gels in about 2 minutes.

The mold is then placed in an oven at 50° C. for 6 days for drying the gel, at the end, the gel is transformed into a xerogel.

At the end of the drying, a shrinkage by a factor 2 is observed in every dimension.

FIG. 2 represents a photograph of the object obtained (portion b)) besides its model (portion a)).

d) Characterization of the Constitutive Xerogel of the Retroreflector

In a first phase, it is preceded with the determination of the porosity of the xerogel. Specifically, this porosity is determined by nitrogen adsorption-desorption at 77K.

The specific surface area developed is 421 m$^2$/g and the porous volume is 0.27 cm$^3$/g.

Given that the measured density of the xerogel is 0.71 g/cm$^3$, the porosity is 0.38.

In a second phase, it is preceded with the measurement of the refractive index. This measurement is carried out by means of a microscope.

To do this, a parallelepiped of dimensions 2 mm*5 mm*10 mm is laid on a glass slide, which is in xerogel made under the same conditions as the constitutive one of the retroreflector.

This glass slide is then deposited on the stage of a microscope.

Next, focusing is performed on the upper face of the glass slide and the value read on the depth vernier is noted, this value being identified hereafter by the index $z_0$.

Next, the focusing is performed on the image of the glass slide through the xerogel and the value read on the depth vernier is noted, this value being identified hereafter by the index $z_1$.

Finally, the focusing is performed on the upper face of the xerogel and the value read on the depth vernier is noted, this value being identified hereafter by the index $z_2$.

The refractive index is obtained with the following equation:

$$n'=(z_2-z_0)/(z_2-z_1)$$

Figure 3:
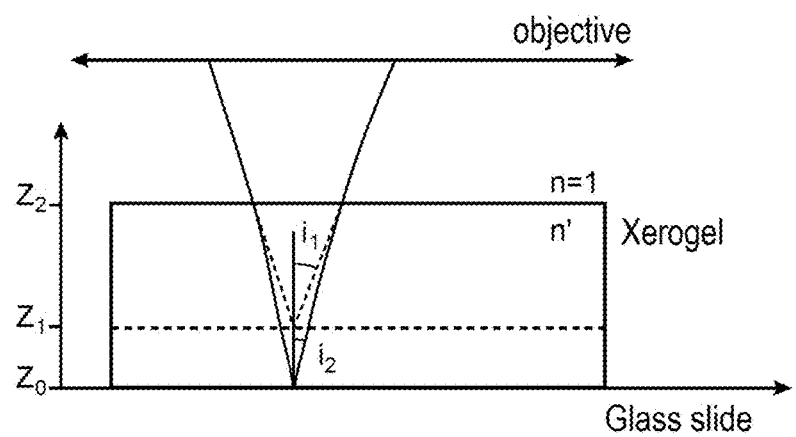
FIG. 3 is a diagram illustrating the principle for measuring the refractive index by means of a microscope.

This equation may theoretically be explained on the basis of FIG. 3, illustrating the optical diagram of the optical index measurement by means of a microscope, this diagram illustrating the path of the rays in the microscope and a vertical axis reporting the values $z_0$, $z_1$ and $z_2$.

From this diagram, the following relationships are established:

$$\tan i1 = \frac{x}{z2-z1}$$
$$\tan i2 = \frac{x}{z2-z0}$$

According to Descartes law (refraction on a planar dioptre), one has:

$$n' = \frac{\sin i1}{\sin i2}$$

For small angles $i_1$ and $i_2$, it is possible to develop to the first order:

$$\tan i = i + o(i)$$
$$\sin i = i + o(i)$$

It is then possible to express the refractive index n' of the xerogel according to $z_0$, $z_1$ and $z_2$:

$$n' = \frac{\sin i1}{\sin i2} \approx \frac{\tan i1}{\tan i2}$$
$$n' = \frac{z2-z0}{z2-z1}$$

Finally, in a third phase, it is preceded with a test in order to observe the retroreflection effect produced by the retroreflector achieved in step c).

Figure 4:
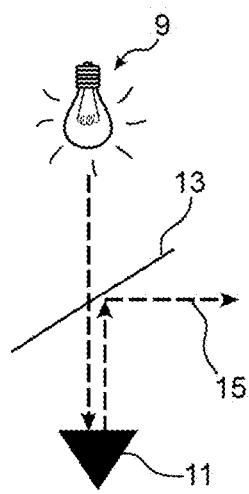
FIG. 4 is a diagram illustrating the experimental mounting allowing measurement of the intensity of the light reflected by a retroreflector.

To do this, as illustrated in FIG. 4, a semi-reflective slide 13 which will allow direction of the retroreflected ray towards a camera device 15, which will record the image from the retroreflection, is interposed between a light source 9 and the retroreflector 11 as illustrated in FIG. 4.

Figure 5:
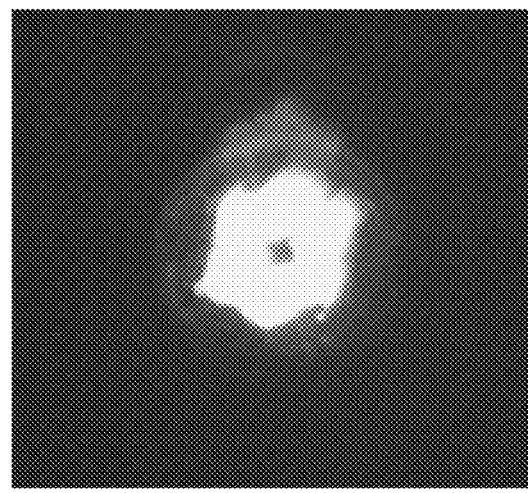
FIG. 5 represents a photograph of the light reflected by the retroreflector obtained in example 1.

This image is reproduced at FIG. 5.

Example 2

This example has the intention of demonstrating the efficiency of the retroreflector prepared in Example 1 for detecting a volatile organic compound (VOC), which is orthonitrophenol (this compound being obtained here from the supplier Sigma Aldrich), which fits the following formula:

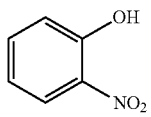

This compound may be emitted after hydrolysis of an enzymatic substrate with a specific enzyme of a microorganism. The detection of such a compound may have a certain interest for indirect detection of microorganisms, as illustrated by the article *Phys. Chem. Chem. Phys*, Vol. 15, no. 38, pages 15840-15844.

Figure 6:
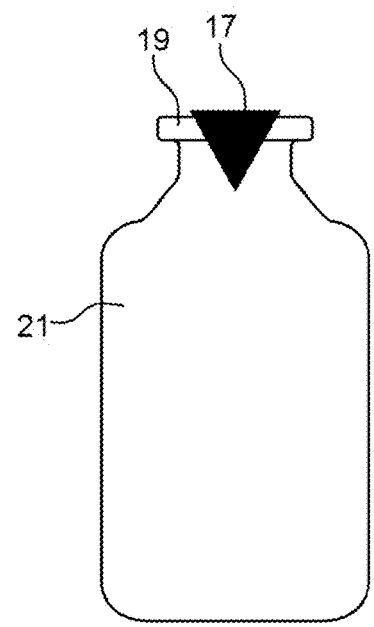
FIG. 6 represents a flask for which it is desired to characterize the inner environment by means of the retroreflector prepared in example 1 placed in a septum closing said flask.

The retroreflector (reference 17) prepared in Example 1 is placed in a septum in rubber (reference 19), which hermetically closes a flask (reference 21) with a volume of 15 mL, as illustrated in FIG. 6.

To do this, the septum is pierced with a dye cutter, in order to obtain a hole with a diameter of 6 mm, which is intended to receive the retroreflector. Once placed on the flask via the septum, the retroreflector has an angular end directed towards the inside of the flask.

In the flask, before the positioning of the septum, 5 mL of an aqueous solution of 2-(N-morpholino)ethanesulfonic acid (obtained from the supplier Sigma Aldrich) is initially introduced, this solution having a pH of 6.1.

In order to be more specific, the orthonitrophenol appears in two forms: a protonated form with a pH of less than 7.2 and a deprotonated form at a pH greater than 7.2. Now only the protonated form is volatile, which explains why it is necessary to buffer the solution at a pH of less than 7.2, in order to be in the presence of the volatile form of orthonitrophenol.

At t=0 second, the flask is closed with the septum equipped with the retroreflector. At t=900 seconds, 5 µL of orthonitrophenol at 0.1 mol/L is then introduced with a syringe crossing the rubber septum, in return for which a solution results having a final concentration of 100 µmol/L.

A fraction of the added orthonitrophenol passes into the gas phase, because of the protonation phenomenon occurring in the flask. The retroreflector captures a portion of the emitted gas. The presence in the retroreflector of amine groups from the precursor 4-aminobutyltriethoxysilane gives the possibility of deprotonating the orthonitrophenol.

The deprotonated form of orthonitrophenol has the property of absorbing at the wavelength of 415 nm ($\varepsilon$=3500 L·mol$^{-1}$·cm$^{-1}$).

In order to follow the variation in the absorption of the retroreflector at 415 nm, the circuit is illuminated with two light-emitting diodes: respectively, one diode emitting at 415 nm and a diode emitting at 590 nm, which is used as a reference.

The intensities of both of these wavelengths are measured by means of a color camera by separating the red-green-blue channels, the intensities being integrated over a region of interest corresponding to a disc, which covers the image of the retroreflector. The intensity at 415 nm is measured on the blue channel while the intensity at 590 nm is measured on the red channel.

Figure 7:
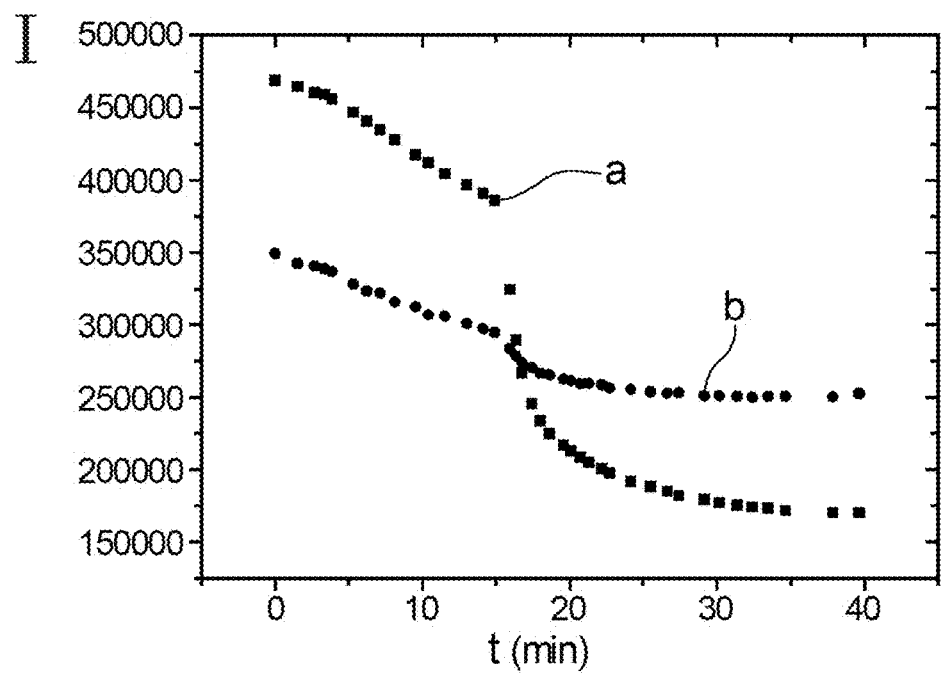
FIG. 7 is a graph illustrating the evolution of the intensity I at 415 nm and at 590 nm versus time t (in minutes) for the retroreflector of example 1 in the presence of orthonitrophenol.

The evolution of the intensity at 415 nm and at 590 nm versus time (in minutes) is illustrated by FIG. 7 (curve a) for the intensity at 415 nm and the curve b) for the intensity at 590 nm).

For the intensity at 590 nm (reference signal), a continuous reduction in the intensity is observed.

For the intensity at 415 nm, it is easily observed that the signal falls behind at 15 minutes, which corresponds to the moment of the injection of the orthonitrophenol into the flask. This therefore certifies the capability of the retroreflectors of the invention of trapping orthonitrophenol in deprotonated form.

The invention claimed is:

1. A retroreflector adapted to be placed in contact with an environment, comprising, as a constitutive material, the material comprised between the faces of the retroreflector and also delimiting the latter, a porous material capturing a parameter of said environment, said parameter of said environment being a gas, said material inducing a modification of the optical transmission properties of the retroreflector in the presence of said parameter, and said retroreflector adapted to receive an incident light beam through a first face and to re-emit a light beam through said first face.

2. The retroreflector according to claim 1, which comprises three first faces, so called rear faces, defining a trihedron, said three faces being convergent in a point forming an apex of the trihedron, and a fourth face, a so called opposite front face to said apex of the trihedron, and containing said trihedron, said material extending between these faces.

3. The retroreflector according to claim 2, wherein each rear face respectively extends along a first plane, a second plane and a third plane, said planes being substantially orthogonal with each other, the light beam emerging along a direction substantially parallel to that of the incident light beam.

4. The retroreflector according to claim 1, which has a cube corner shape.

5. The retroreflector according to claim 1, wherein the porous material is a material with open porosity.

6. The retroreflector according to claim 1, which has a refractive index ranging from 1.2 to 2.

7. The retroreflector according to claim 1, which has a refractive index ranging from 1.66 to 2.7.

8. The retroreflector according to claim 1, wherein the constitutive material is an organic or inorganic material, comprising, inside it, one or several compounds bearing one or several groups fulfilling a function for capturing a parameter of the environment.

9. The retroreflector according to claim 8, wherein the organic material is a material comprising at least one polymer.

10. The retroreflector according to claim 8, wherein the inorganic material is a material of the inorganic oxide(s) type.

11. The retroreflector according to claim 10, wherein the material of the inorganic oxide(s) type is a material of the oxide(s) type of a metal element and/or of a metalloid element.

12. The retroreflector according to claim 10, wherein the material of the inorganic oxide(s) type comprises one or several oxides of an element selected from among silicon, titanium, zirconium, aluminium, vanadium, chromium, yttrium, tungsten, niobium, molybdenum.

13. The retroreflector according to claim 10, wherein the material of the inorganic oxide(s) type comprises silica and an oxide selected from among zirconia, titanium oxide.

14. The retroreflector according to claim 10, wherein the material of the inorganic oxide(s) type is a material obtained via a sol-gel method.

15. The retroreflector according to claim 8, wherein the compound(s) bearing one or several groups are included in the organic or inorganic material without being covalently bound to the latter.

16. The retroreflector according to claim 8, wherein the compound(s) bearing one or several groups are covalently bound to said organic or inorganic material.

17. The retroreflector according to claim 8, wherein, when the parameter of the environment is a chemical compound in the form of a gas, the compound(s) bearing one or several groups fulfilling a function for capturing a parameter of the environment have one or several groups able to capture said chemical compound with chemical modification of the latter and/or able to capture said chemical compound by chemical affinity without any chemical modification of the chemical compound.

18. The retroreflector according to claim 17, wherein, when the parameter of the environment is a chemical compound able to chemically modify the compound(s) comprised in the material, the chemical modification results from an acid-base reaction between the chemical compound and the group(s) of the compound(s) comprised in the material.

19. The retroreflector according to claim 17, wherein, when the parameter of the environment is a chemical compound which has chemical affinity for the compound(s) comprised in the material, the group(s) of the compound(s) comprised in the material are hydrophobic groups, when the chemical compound comprises a hydrophobic group, such as a hydrocarbon group, or are hydrophilic groups, when the chemical compound comprises a hydrophilic group, such as an OH group.

20. The retroreflector according to claim 8, wherein the compound(s) bearing one or several groups fulfilling a function for capturing a parameter of the environment are selected from among:
    compounds belonging to the category of pH colored indicators;
    compounds belonging to the category of solvatochromic probes;
    organic compounds belonging to the family of aldehydes;
    organic compounds belonging to the family of disulfides;
    organic compounds belonging to the family of primary amines;
    organic compounds belonging to the family of carboxylic acids; and
    organic compounds belonging to the family of ketones.

21. A method for detecting the presence or the absence of at least one parameter of the environment, which is a gas, comprising the following steps:
    a step for putting into contact a retroreflector as defined according to claim 1, with said environment;
    a step for illuminating the retroreflector with a first light beam having a first wavelength, said first wavelength corresponding to a wavelength which causes a variation in the optical transmission of the material making up the retroreflector, when the material captures the parameter of the environment;
    a step for analyzing a first light beam reflected by the retroreflector, from which is inferred the presence or the absence of said parameter of the environment.

22. The detection method according to claim 21, further comprising the following steps:
    a second step for illuminating the retroreflector with the light beam comprising a second wavelength, said second wavelength corresponding to a wavelength which causes a second variation of the optical transmission of the material making up the retroreflector when the material captures the parameter of the environment, said second variation being less than said first variation;
    a step for analyzing a second light beam reflected by the retroreflector;
    a step for comparing said first and second reflected beams, from which is inferred the presence or the absence of the parameter of the environment.

23. The detection method according to claim 21, wherein:
    the first light beam includes a plurality of wavelengths;
    the step for analyzing the reflected beam comprises an analysis of said beam at least two wavelengths from said plurality of wavelengths.

* * * * *